(12) United States Patent
Callede et al.

(10) Patent No.: US 9,113,856 B2
(45) Date of Patent: Aug. 25, 2015

(54) DEVICE FOR TAKING AT LEAST ONE SAMPLE OF TISSUE

(75) Inventors: David Callede, Sarlar la Caneda (FR); Denis Pinaud, Draillant (FR); Adrien Moine, Evian (FR); Laurent Pivard, Dortan (FR); Fabrice Teppe, Oyonnax (FR)

(73) Assignee: Coloplast A/S, Humlebaek (DK)

( * ) Notice: Subject to any disclaimer, the term of this patent is extended or adjusted under 35 U.S.C. 154(b) by 236 days.

(21) Appl. No.: 13/809,908

(22) PCT Filed: Jul. 15, 2011

(86) PCT No.: PCT/DK2011/050284
§ 371 (c)(1),
(2), (4) Date: Jan. 14, 2013

(87) PCT Pub. No.: WO2012/007011
PCT Pub. Date: Jan. 19, 2012

(65) Prior Publication Data
US 2013/0116594 A1 May 9, 2013

(30) Foreign Application Priority Data

Jul. 16, 2010 (EP) .................................. 10290406
Oct. 25, 2010 (EP) .................................. 10188672

(51) Int. Cl.
*A61B 10/02* (2006.01)
*A61B 17/00* (2006.01)
*A61B 19/00* (2006.01)

(52) U.S. Cl.
CPC ......... *A61B 10/0233* (2013.01); *A61B 10/0275* (2013.01); *A61B 2010/0208* (2013.01); *A61B 2017/00367* (2013.01); *A61B 2017/00393* (2013.01); *A61B 2019/304* (2013.01)

(58) Field of Classification Search
CPC ............... A61B 10/02; A61B 10/0233; A61B 10/0275; A61B 10/0266; A61B 2010/0208
USPC .................. 600/562, 566, 567, 583; 606/167, 606/181–186
See application file for complete search history.

(56) References Cited

U.S. PATENT DOCUMENTS 4,699,154 A * 10/1987 Lindgren ...................... 600/567
4,953,558 A * 9/1990 Akerfeldt ...................... 600/564
5,655,542 A * 8/1997 Weilandt ....................... 600/567

(Continued)

FOREIGN PATENT DOCUMENTS

EP 1649814 A1 4/2006
WO 2007074123 A1 7/2007

*Primary Examiner* — Devin Henson
*Assistant Examiner* — David J McCrosky
(74) *Attorney, Agent, or Firm* — Coloplast Corp., Coloplast A/S; Nick Baumann

(57) ABSTRACT

A device for taking a sample of soft tissue from an organ includes a body, a needle having a cannula coaxial with a stylet, a mechanism for arming the needle, a triggering mechanism to release the stylet, and a security element. The mechanism includes an arming button connected to a platform. A distal portion of the platform is wider than a proximal portion of the platform. The platform includes a curvilinear edge connecting the distal portion of the platform with the proximal portion of the platform. The curvilinear edge of the platform is configured to interact with a projection formed inside of the body to pivot the platform out of a first position aligned with a cannula slide into a second position aligned with a stylet slider.

11 Claims, 5 Drawing Sheets

(56) References Cited

U.S. PATENT DOCUMENTS

| | | |
|---|---|---|
| 5,842,999 A | 12/1998 | Pruitt et al. |
| 7,153,275 B2 | 12/2006 | Blondeau |
| 7,229,419 B2 * | 6/2007 | Hancock .................. 600/567 |
| 2008/0281226 A1 * | 11/2008 | Peters ..................... 600/567 |

* cited by examiner

DEVICE FOR TAKING AT LEAST ONE SAMPLE OF TISSUE

TECHNICAL FIELD

The present invention relates to a device for taking at least one sample of soft tissue from an organ, said device comprising a body and a needle arranged in the body and extending at least partly outside the body through the front end of the body, the needle is formed by a stylet and a cannula coaxial with said stylet, said device comprising a mechanism for arming the needle, designed for sequentially moving the stylet and then the cannula from a rest position to a shooting position wherein the stylet and the cannula are retracted towards the rear end of the body, and a triggering mechanism designed to release the stylet then the cannula and to allow their displacement from the shooting position to the rest position, the cannula being coupled to a cannula slider comprising at least one retaining element for engaging with the cannula slider in a shooting position, the stylet being coupled to a stylet slider comprising at least one retaining element for engaging with the stylet slider in a shooting position and means for unlocking the cannula slider.

BACKGROUND ART

Nowadays, there are several devices for taking samples of soft tissue, these devices being generally used to extract, in a minimally invasive way, a sample of an organ from a human being or an animal for analysis purpose. This extraction operation is generally known as biopsy and the device used is known as a biopsy gun.

Such a sampling device comprises in particular a sampling needle formed by a cannula and a stylet, an arming mechanism placed on a body and a trigger also placed on the body of the device.

The arming mechanism is used to partially retract the needle towards the inside of the body of the device. The device is placed near the organ from which a sample is to be taken, and then the trigger is pressed so that the needle can penetrate into the organ. The needle being formed by a stylet and by a cannula, the stylet penetrates into the organ, then the cannula covers the stylet. The stylet comprises at least one notch receiving the tissue sample to be taken. When the cannula covers the stylet, the tissue sample is trapped in the notch and is cut. The unit is withdrawn so that the sample(s) arranged between the stylet and the cannula can be removed. An example of application of such a device is taking tissue samples from the prostate.

The arming of the needle is generally achieved in two steps, namely the arming of the cannula in a first step and the arming of the stylet in a second step.

During sampling of tissues, it is common for the person carrying out the sampling to have only one free hand, while the other hand is being used to hold other medical devices, such as for example an echographic probe. In this case, it is important to be able to manipulate the sampling device with one single hand. Here, the handling includes the arming of the cannula, the arming of the stylet and the release of the shot allowing the sample to be taken.

An example of existing devices which enable handling with one single hand is described in the U.S. Pat. No. 7,153,275. This device is perfectly functional if handled correctly as in most cases. However, incorrect handling may cause problems. In particular, when the arming of the cannula or the stylet has not been achieved correctly, the shot can be unintentionally released. In particular, this can cause problems if a shot is released before the device is correctly placed near the organ from which a sample is to be taken.

Another problem known with this kind of device is that incorrect handling of the arming mechanism may cause the shooting mechanism to become totally jammed, thus rendering the device unusable.

The following description describes a tissue sampling device which has the advantages of the devices of the prior art i.e. it is possible to use this device with one hand. However, this device does not have the drawbacks of the systems of the prior art. Thus, even in the case of incorrect handling, the shot is not released unintentionally. Moreover, the device cannot be jammed as a result of incorrect handling.

DISCLOSURE OF THE INVENTION

An object of the invention is fulfilled by a sampling device as defined in the preamble and characterized in that the mechanism for arming the cannula further comprises means for separating the means for unlocking the cannula slider and said retaining element for engaging with the cannula and at least one security element designed for engaging with the stylet slider in a position in which the means for unlocking the cannula slider are separated from the retaining element for engaging with the cannula slider in a shooting position.

According to the present invention, the device for taking samples may easily be manipulated with one hand. To achieve this, the device comprises a body having an essentially cylindrical shape that can be easily held. It also comprises a sliding arming button, which is positioned on the body so that this button can be easily moved using one finger. This arming button is connected to an arming mechanism, which has two different functions. In a first step, the displacement of the arming button has the effect of moving the cannula towards the back of the body as well as moving the stylet several millimeters. When the cannula has been displaced to the desired position, the arming button is released, allowing it to return to its initial position. When it is operated again, the arming button has a different function than the previous one. In a second step, it is used to move the stylet towards the back of the body. Owing to the mechanism of the invention, the user carries out the same displacement movement of the arming button twice, these two movements having different effects.

This way of proceeding has the advantage of enabling a body of relatively small length to be provided, thus only requiring a displacement of the arming button corresponding to the displacement of the user's finger, without the user having to change the position of his/her hand.

The device of the invention makes it possible to avoid the unintentional triggering of a shot. Such an unintentional shot can occur in the devices of the prior art, in particular, when the arming of the cannula has not been made correctly.

In the present invention, the biopsy gun comprises two security systems. One of them prevents involuntary activation of the trigger, thus preventing the biopsy gun from shooting unintentionally. The other prevents an unintentional shot due to incorrect arming. To achieve this, the mechanism for arming the cannula cooperates with a security mechanism. This cooperation provides a guarantee that if the security mechanism is not activated, the arming is not achieved. If the security mechanism is activated, an unintentional shot cannot occur. Thanks to this, there is no risk that a shot is released accidentally.

By virtue of the geometry of the device, the elements which enable the guidance of the stylet and the cannula, as well as the propulsion and retaining elements for the stylet and the cannula are arranged symmetrically around a longitudinal axis materialized by the stylet. This ensures that there are few transversal forces. Such transversal forces have the effect of increasing the friction between the parts, of causing wear and of risks of rupture as well as of jamming. By suppressing these transversal forces, it is possible to use smaller springs as it is no longer necessary to overcome friction. The biopsy gun is thus easier to use since the arming is made easier. Moreover, more samples may be taken using the gun, since the jamming risk is reduced.

Having symmetrical retaining elements for the stylet and the cannula ensures a greater security, since at least two elements retain the stylet and the cannula. Moreover, in case of an asymmetrical retaining element, a force can act on the retaining element and possibly deform it and/or unhook it. This can lead to jamming, ruptures or an unintentional shot.

BRIEF DESCRIPTION OF THE DRAWINGS

This invention and its advantages will be better understood with reference to the enclosed drawings and to the detailed description of a particular embodiment, in which.

BEST MODE FOR CARRYING OUT THE INVENTION

Figure 1:
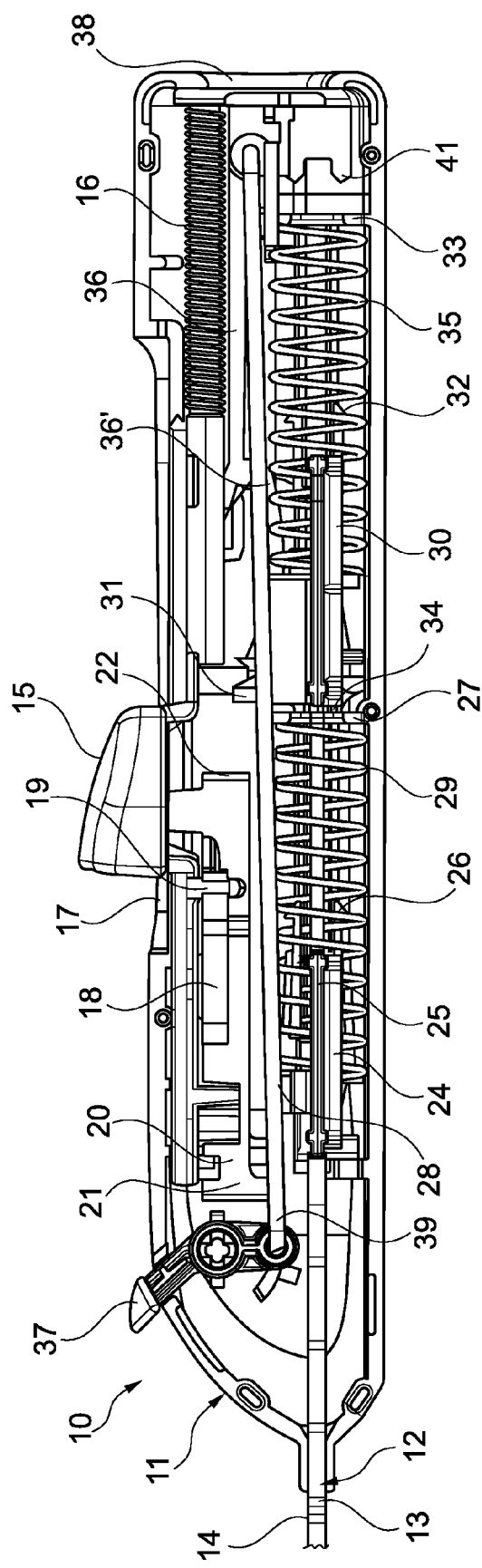
FIG. 1 is a partial cross-sectional view of one embodiment of a device for taking a sample of tissue.

With reference to the drawings, the sampling device 10 according to this invention essentially comprises a body 11 and a needle 12. The needle is formed by a stylet 13 and a cannula 14. The stylet comprises a tip, allowing the needle to penetrate into the organ from which one wishes to take a sample. Furthermore, the stylet comprises at least one notch (not shown). In practice, the stylet 13 comprises a notch that enables a sample to be taken. The cannula 14 slides around the stylet 13 and is used on one hand to cut the tissue into which the stylet has penetrated and on the other hand to keep the tissue sample taken in place when removing the needle from the organ.

The body 11 essentially comprises an arming mechanism arranged to arm the needle 12 and a triggering device arranged to release a shot of the needle for the intended sampling. More particularly, the arming of the needle is carried out in two steps, namely a step of arming the cannula 14 and a step of arming the stylet 13.

The sampling is made by a shot of the needle. Such a shooting also comprises two steps, namely a displacement step of the stylet 13 under the effect of a propelling power of the stylet, then a displacement step of the cannula 14 under the effect of a propelling power of the cannula. Releasing a shot is achieved by releasing the displacement of the stylet. The displacement of the cannula is a consequence of the release of the stylet as it will be explained in detail below.

In practice, the mechanism for arming the cannula and the mechanism for arming the stylet use only one arming button 15 which acts differently depending on whether the arming of the cannula has already been carried out or not. The arming button cooperates with a return spring 16 of the arming button, the spring having the function of bringing back the arming button 15 to the rest position, i.e. towards the front of the body, when it is not manipulated.

The body of the device is formed by two parts which, once assembled, comprise guidance grooves intended to ensure the displacement of the parts. The body also comprises a slit 17 in which the arming button moves.

With reference to the figures, the arming button 15 cooperates with a platform 18. This platform can pivot around a platform axis 19 integral with the arming button. One of the ends of the platform, located near the front end of the sampling device, i.e. the needle-end of the sampling device, comprises a widened zone 20, each end of this widened zone including a finger 21 whose function is described in detail below. The rear end of the platform comprises a pushing device 22 whose function is also described in detail below.

Figure 9:
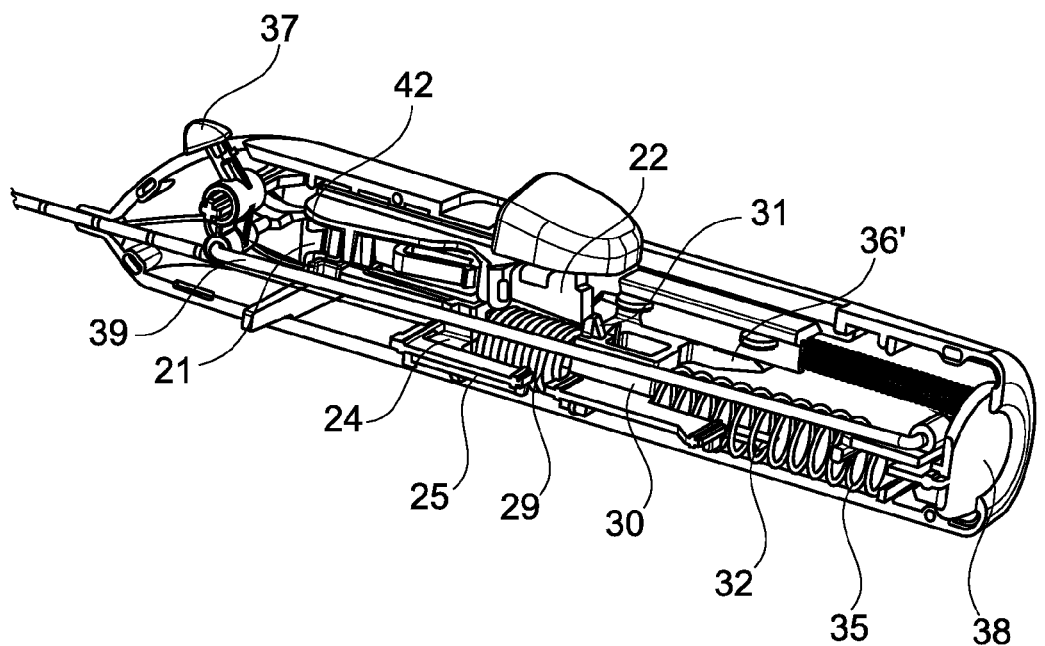
Figure 10:
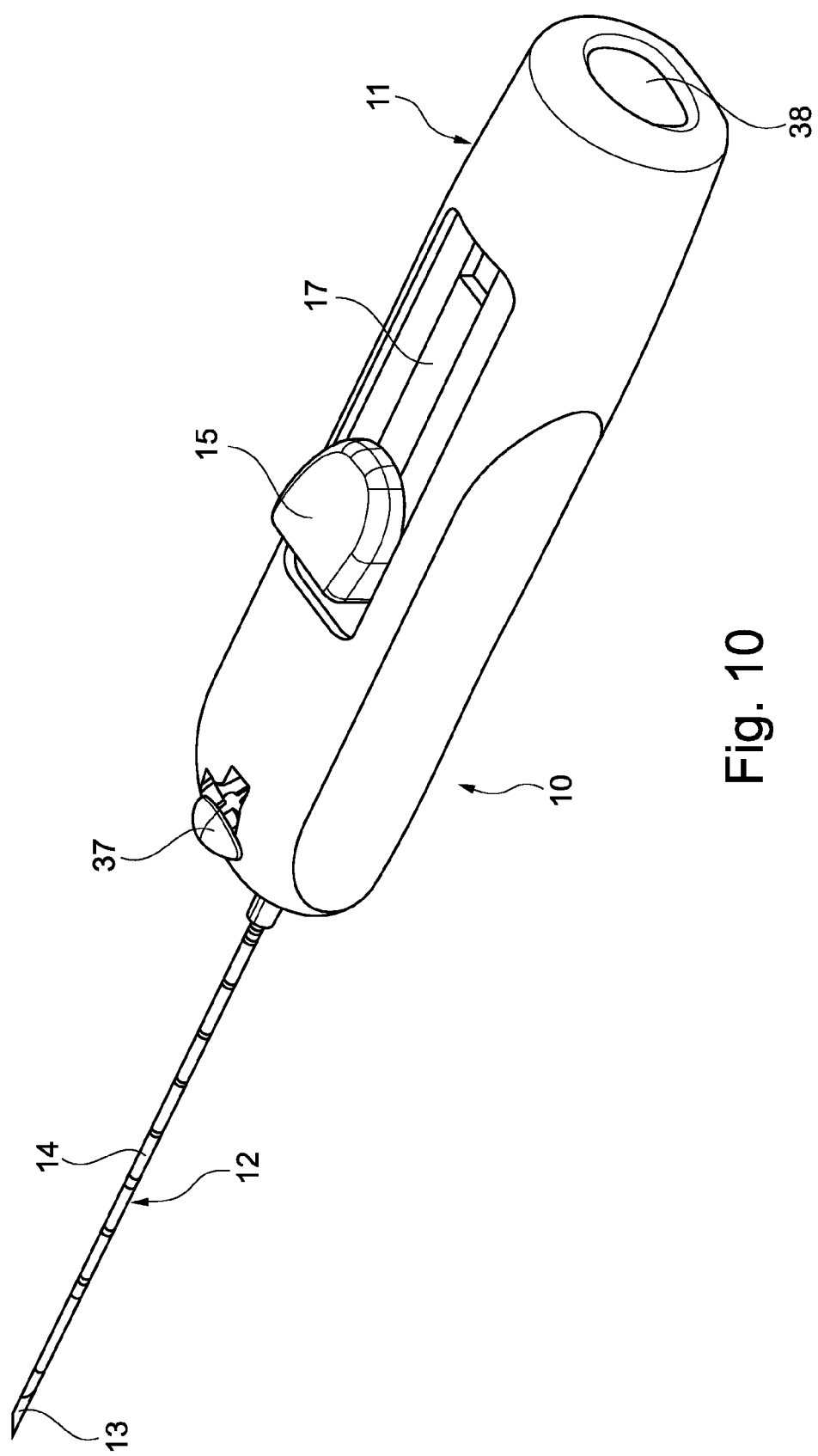
FIG. 10 is a perspective view of the device of the invention.

The platform 18 is connected to the arming button 15 by the platform axis 19 and by a return device (not shown). This return device may be a spring or an elastic tab which has the function of keeping this platform in a predefined position called a rest position. This rest position is visible in particular in FIG. 9.

The mechanism for arming the cannula 14 is intended to move the cannula into the shooting position. This cannula is coupled to a cannula slider 24. According to one advantageous embodiment, the cannula slider 24 comprises two fins 25 disposed in a plane also containing the cannula. These two fins 25 cooperate with two guide grooves provided in the body of the device so as to ensure an effective sliding motion of the cannula slider 24. This slider comprises, at its rear end, a retaining element 26 of the cannula slider. According to an advantageous embodiment, the retaining element is formed by two hooks. Advantageously, these hooks are symmetrical and have a certain flexibility, which allows for them to be hooked onto a retaining device 27 of the cannula slider and to be unhooked from this device by bringing the hooks together. It is also possible to use only one hook or several hooks arranged asymmetrically.

Furthermore, the cannula slider 24 comprises a spur 28 cooperating with one of the fingers 21 of the platform. The cannula slider cooperates with a spring 29 for the propulsion of the cannula slider, which is arranged between the cannula slider 24 and the retaining device 27 of the cannula slider. This spring 29 is designed to supply the required force to propel the cannula slider towards the front of the body. The displacement of the cannula slider towards the back of the body compresses the spring.

The mechanism for arming the stylet is intended for the displacement of the stylet into the shooting position, this displacement being achieved after the cannula 14 has been armed. To that effect, the stylet 13 is coupled to a stylet slider 30, which comprises a spur 31 near its front end and a retaining element 32 at its rear end. As for the cannula slider, the retaining element 32 can be formed by two partially elastic hooks. It can also be formed only by one hook or by several hooks arranged symmetrically or asymmetrically.

The retaining element 32 can be hooked on a retaining device 33 of the stylet slider and can be unhooked from this device by approaching the hooks to each other.

Similar to the cannula slider, the hooks of the stylet slider are sufficiently flexible to be deformed towards each other and sufficiently rigid to provide adequate support.

The stylet slider 30 comprises, at its front end i.e. at the side of the cannula slider 24, means for unlocking 34 the cannula slider formed for example by two inclined planes.

The stylet slider 30 cooperates with a spring 35 for the propulsion of the stylet slider, which is placed between the stylet slider 30 and the retaining device 33 of the stylet slider. This spring is designed to supply the required force to propel the stylet slider 30 towards the front of the body. The displacement of the stylet slider towards the back of the body compresses the spring.

The device of the invention further comprises a security element 36 which can advantageously be formed by a security hook cooperating with a rear shoulder 36' of the stylet slider and with the spur 31 of this slider.

The device according to the invention further comprises a triggering device. According to an advantageous embodiment, this triggering device comprises two triggers 37, 38 connected to each other by a rod 39. One of the triggers 37 is placed in the front of the body, in front of the arming button 15, and the other trigger 38 is placed in the rear of the body. The rear trigger 38 is associated with a return spring of the trigger, designed to bring the trigger back in the original position after it has been pressed. This enables the user to easily access the triggering mechanism, whatever the position of the hand when using the device.

The rear trigger 38 comprises means for unlocking 41 the stylet slider formed by two elements arranged in inclined planes.

The sampling device according to this invention operates in the following way. Let us suppose that the initial position is a position in which the cannula 14 and the stylet 13 are maximally extended towards the outside of the body 11 of the device. This position corresponds to the normal position of the device when it is not going to be used, i.e. the rest position. This position is shown in FIG. 1.

Figure 2:
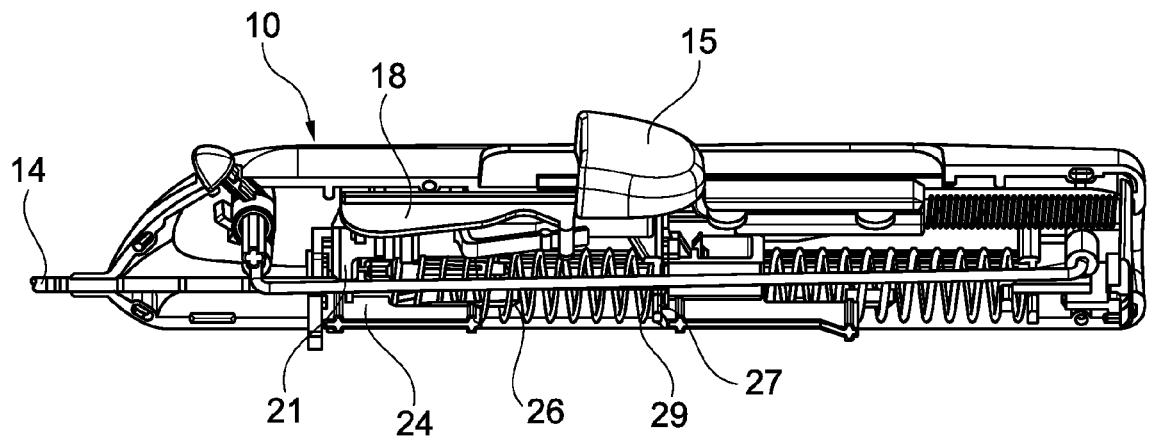
FIG. 2 is a partial cross-sectional view of the device illustrated in FIG. 1.
Figure 3:
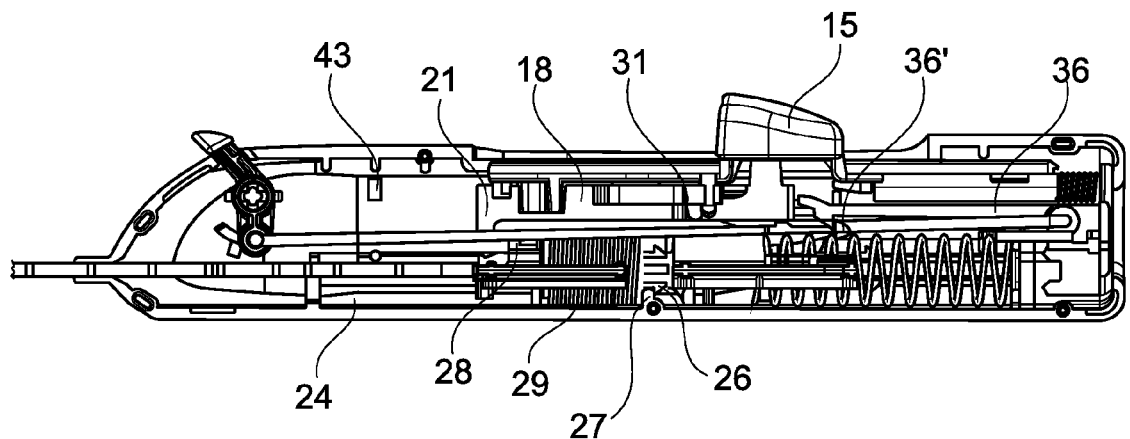
FIG. 3 is a partial cross-sectional view of the device illustrated in FIG. 1.
Figure 4:
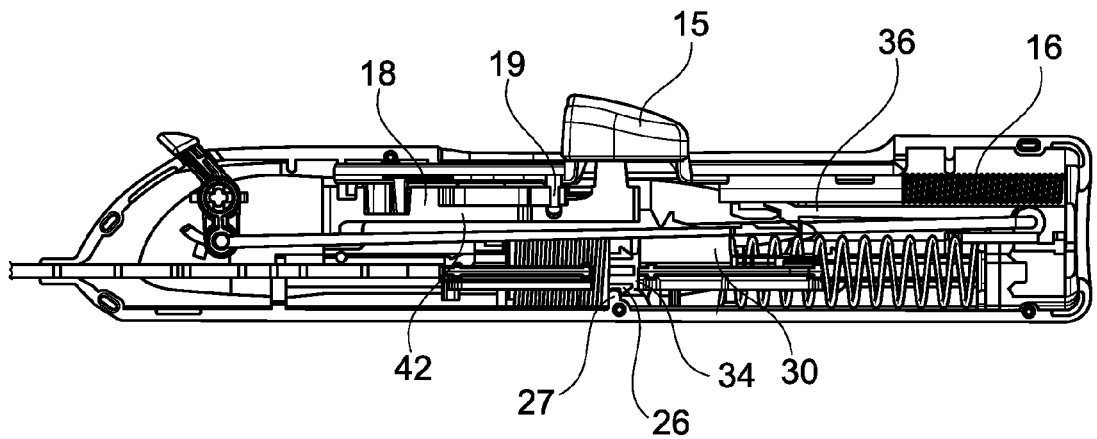
FIG. 4 is a partial cross-sectional view the device illustrated in FIG. 1.

In a first step, the arming of the cannula 14 is carried out. During this operation, the user actuates the arming button 15, sliding it towards the back of the device 10. The platform 18 being integral with the arming button 15, the displacement of the latter also draws the platform backwards. One of the fingers 21 of the platform 18 comes in contact with the spur 28 placed towards the front end of the cannula slider 24 (FIG. 2). The latter is thus displaced backwards, against the force of the spring 29 for the propulsion of the cannula slider. This movement is carried out until the retaining elements 26 of the cannula slider 24 enter into contact with the retaining device 27 for the cannula slider. The retaining elements of the cannula 24 may be formed as hooks and the retaining device 27 may for example be a ring provided in the body of the device The ring comprises a central hollow in which the ends of the hooks of the cannula slider pass. These hooks lean on the back face of the ring and engage with the cannula slider 24 against the force of the propulsion spring of the cannula slider. This position is shown in FIG. 3.

At the end of the displacement of the platform, i.e. just before the retaining elements 26 of the cannula slider go into engagement with the corresponding retaining device 27, the platform 18 comes into contact with the spur 31 of the stylet slider and displaces the latter slightly backwards. Following this displacement, the hook forming the security element 36 cooperates with the rear shoulder 36' of the stylet slider and retains the slider in this position by preventing it from moving forward.

The end of the displacement of the platform also has the effect of displacing the cannula slider 24 into a position so that the retaining element 26 of the cannula slider goes into engagement with the retaining device 27 of the cannula slider.

When the stylet slider 30 is retained by the security hook, the unlocking means 34 being part of the stylet slider 30, or in other words, the means for unlocking the cannula slider, cannot move sufficiently forward to separate the hooks of the cannula slider from the retaining organs 27 of these hooks. In this way, if when arming the cannula is not retracted to the correct position towards the rear of the body, the hooks of the cannula slider do not hook to the corresponding retaining device, which is immediately detected by the user who simply needs to restart the arming of this cannula. If the arming of the cannula has been carried out correctly, the hooks of the retaining device are maintained in place and the hook of the security element 36 cooperates with the stylet slider 30 so as to prevent it from advancing beyond a predetermined position. In this way, an unintentional release of the shot is not possible.

When the arming of the cannula is completed, the arming button 15 is released. It returns to its initial position towards the front of the device, under the effect of the return spring 16 of the arming button.

During the forward displacement of the platform 18, following the forward displacement of the arming button 15, a ramp 42 of the platform comes into contact with a plug 43 provided in the body. This ramp has the effect of rotating the platform 18 around the platform axis 19, against the force of the return device of the platform. It should be noted that according to this embodiment, it is also possible to provide for the return device of the platform to be constrained before the arming of the cannula and to be released when the arming of the cannula is completed.

Figure 5:
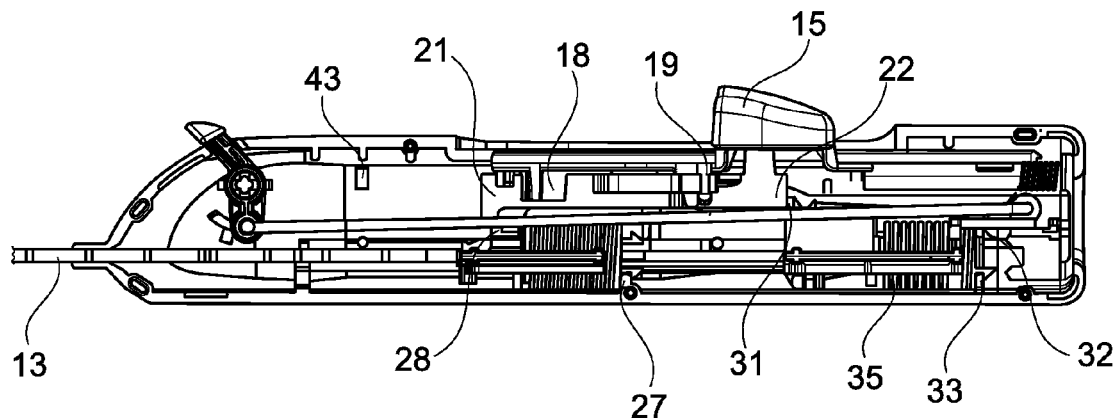
FIG. 5 is a partial cross-sectional view the device illustrated in FIG. 1.
Figure 8:
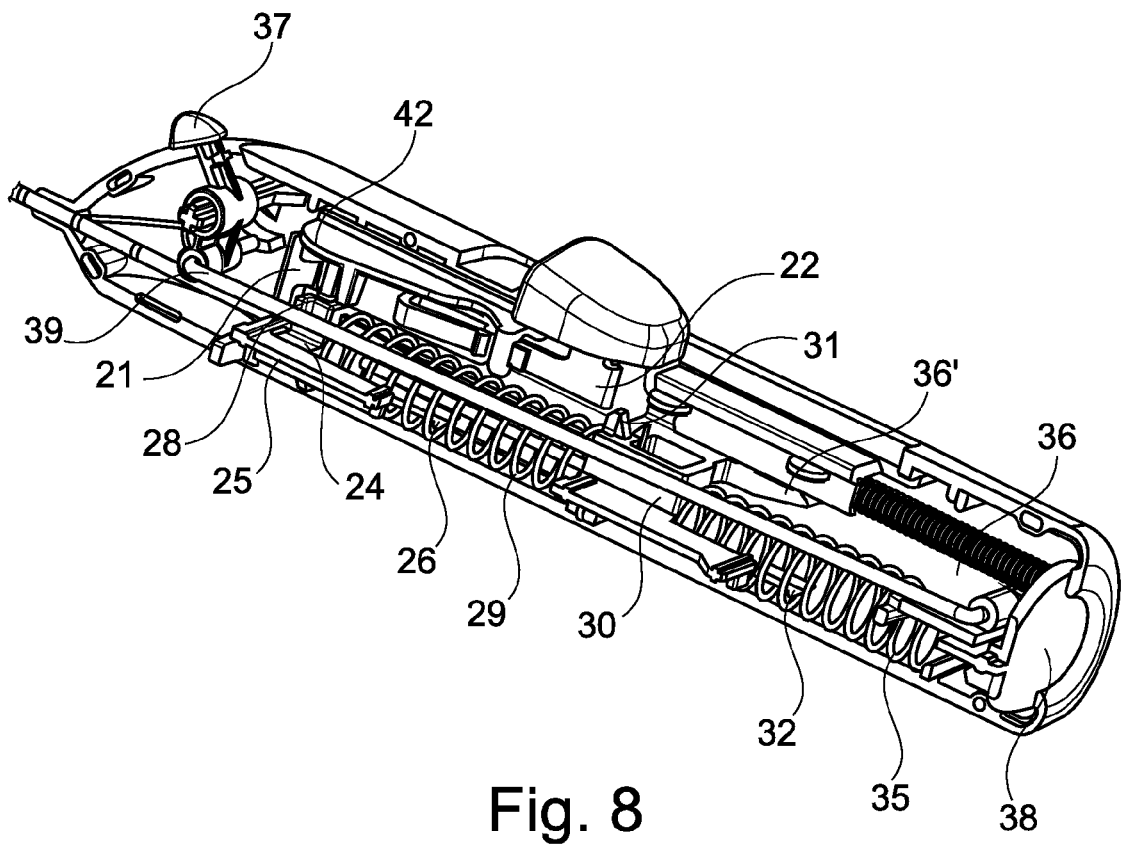
FIGS. 8 and 9 are perspective views of the device of the invention in two different positions.

For the arming of the stylet 13, the arming button 15 is displaced backwards again. However, the platform 18 is no longer in the initial position. The latter has pivoted around the platform axis 19, as the ramp 42 of the platform has been displaced by the support against the plug 43. By this rotation, on one side the finger 21 of the platform does not come into contact with the spur 28 of the cannula slider, and on the other side, the pushing device 22 of the platform leans against the spur 31 of the stylet slider. The rotation of the platform 18 is particularly visible when comparing FIGS. 8 and 9. In FIG. 8, the pushing device 22 is placed next to the spur 31, while in FIG. 9, the pushing device 22 rests against the spur 31. The stylet slider is thus displaced towards the back of the device, against the force of the spring 35 for propelling the stylet slider, until the retaining elements 32 of the stylet slider are arranged in the retaining device 33 for the stylet slider. The retaining device 33, for example in the shape of a ring, is similar to the retaining device 27 for the cannula slider, and the retaining elements 32, for example in the shape of hooks, are similar to the retaining elements 26 of the cannular slider. Advantageously, by providing the retaining device for the stylet slider in the form of a ring and the retaining elements of the stylet slider as hooks, coupling is easily and effectively provided as the hooks engage the ring through the hole. This is shown in FIG. 5.

Figure 6:
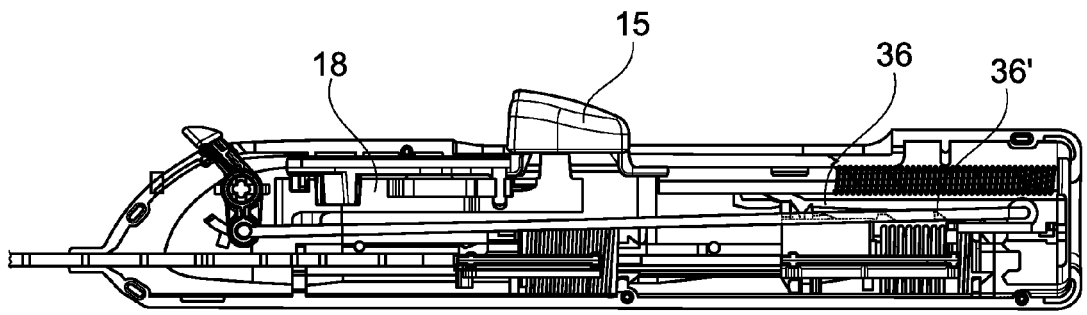
FIG. 6 is a partial cross-sectional view of the device illustrated in FIG. 1.

At this stage, the device is triggered out and ready for the shot. The device is stable in the sense that the cannula and stylet slider hooks are maintained against the corresponding retaining elements. The hook of the security element 36 is no longer in contact with the rear shoulder 36' of the stylet slider. The arming button 15 is released and returns to its initial position under the effect of the return spring of the arming button. The platform 18 also returns to its initial position. This is shown in FIG. 6.

If the arming of the stylet is not carried out correctly and the hooks of the cannula slider are not correctly engaged with the corresponding retaining device, the stylet slider moves in the direction of the cannula slider. The security element 36 cooperating with the rear shoulder 36' of the stylet slider prevents the unlocking means 34 connected to this stylet slider (or means for unlocking of the cannula slider) from interacting with the retaining element 26 of the cannula slider. Thus, even in case of incorrect handling during the arming of the stylet, an unintentional shot cannot be released.

When the needle is armed, the sampling is started by a shot. This shot can be started by means of one of the triggers 37, 38. According to an advantageous embodiment, a security mechanism is provided for preventing a shot during an involuntary manipulation of one of the triggers and in particular of the front trigger. Before the release of the shot, it is necessary to laterally displace this front trigger 37 in relation to the body 11 in order to remove the security function of the mechanism. After the shot, it is necessary to laterally re-displace the front trigger 37 in order to reactivate the security function. This security is manual in the sense that the user has the choice to activate the function by displacing the trigger, or not to activate it.

To release the shot, it is necessary to press one of the triggers 37, 38, the front or the rear one. Actually, in the disclosed embodiment, the shot is always released by a displacement of the rear trigger 38. However, the front trigger and the rear trigger being linked by the rod 39, a pressure on the front trigger will result in the rear trigger being moved forward under the pressure of the rod. Thus, the mechanism can be used by pressing either the rear trigger or the front trigger.

Figure 7:
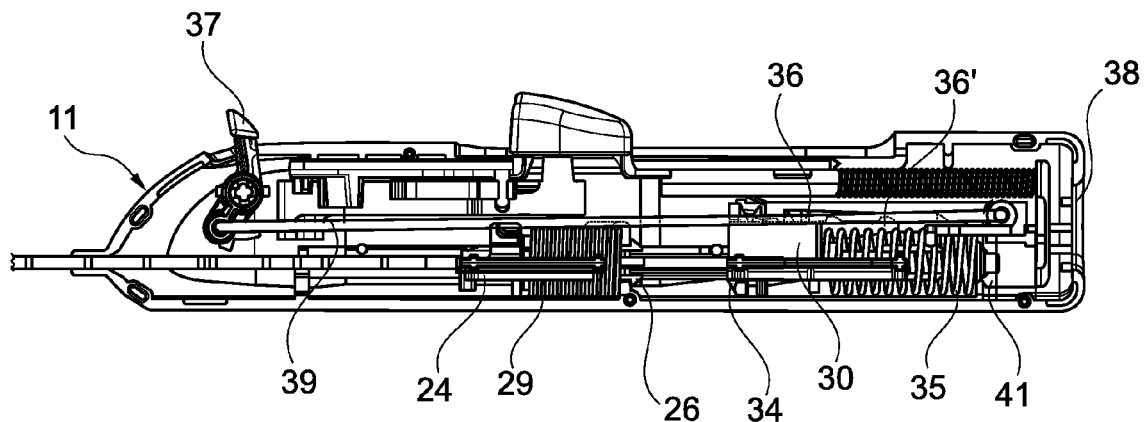
FIG. 7 is a partial cross-sectional view of the device illustrated in FIG. 1.

When the rear trigger 38 is pressed, the unlocking means 41 being part of the rear trigger (or means for unlocking the stylet slider) comes into contact with the hooks of the stylet slider and displaces them towards each other. In this way, they are released from the retaining device 33 of the stylet slider. The slider 30 is propelled forward under the effect of the propulsion spring 35 of the stylet slider. This is shown in FIG. 7.

As the hook of the security element 36 is integral with the rear trigger 38, the fact of displacing this trigger forward also has the effect of displacing the security hook forward and upward. Thus, the stylet slider 30 is no longer retained by this hook and can advance far enough so that the unlocking means 34 being part of this stylet slider come into contact with the hooks 26 of the cannula slider 24.

The means 34 for unlocking the cannula slider comes into contact with the hooks of the cannula slider, presses these hooks towards the centre and releases the retaining elements 27 of the cannula slider. The cannula slider 24 advances under the effect of the propulsion spring 29 of the cannula. This slider advances until it arrives at a stop provided in the body of the device. At this stage, the shot is completed and the device can be withdrawn from the organ from which samples have been taken.

After the arming of the stylet, the platform 18 has returned to its rest position under the effect of the return device of the platform. After the shot, the pieces composing the device return to their initial positions. The sample taken is confined between the stylet 13 and the cannula 14, in the notch provided for this purpose. The sample can be retrieved by retracting the cannula, for example by carrying out an arming movement as previously explained. When the arming of the cannula is completed, it is possible to retrieve the sample without any risk because an unintentional shot is not possible. If a new sampling has to be carried out, the arming button is operated so as to arm the device completely and make it ready for the shot. If it is not necessary to take a new sample, the arming is carried out as well and a blank shot is made to ensure that the device is not armed when discharging it.

The present invention has several advantages in comparison with the devices of the prior art. In particular, by the setup of the retaining elements 26, 32 of the stylet and cannula sliders, it is possible to provide at least two symmetrical hooks. The forces applied on these hooks to hold them by the retaining means as well as during their unhooking during a shot are symmetrical. On the one hand, this ensures that there is no flexion and/or twist on the needle and on the other hand, this enables a safer support of the hooks.

According to an advantageous embodiment, the needle is off-center towards the bottom of the device 10. This enables the use of the device in an easier way with another apparatus as for example an echographic probe.

In case of incomplete movement during the arming of the cannula, the hooks of the cannula slider do simply not engage with the corresponding retaining device. This has the advantage that an unintentional shot is not possible and that the arming of the stylet is not possible if the arming of the cannula is not done correctly.

The device according to the invention can be operated by one single hand since the arming of the cannula and the arming of the stylet use the same arming button.

By the symmetrical construction of the retaining elements of the cannula and stylet sliders and by the position of the propulsion springs of these sliders, the stresses are divided symmetrically around the axis of the needle. Thus, the risks of jamming between the stylet and the cannula are minimized, which enables the device to be used several times and thus allows for a greater number of samples to be taken.

The reduction of the jamming risk allows for the reduction of the force of the propulsion springs while maintaining a high displacement speed for the sliders. This is advantageous for the user because a smaller force is required for arming the device. The handling with a single hand is easier in this way.

Using guide grooves provided in the body of the device and slider fins moving in these grooves also ensures an optimal guidance and reduces the jamming risk.

The invention claimed is:

1. A device configured to take a sample of soft tissue from an organ, the device comprising;
   a body and a needle arranged in the body, the needle extending in a distal direction out of the body, with the needle located at a front end of the body, and the needle is formed by a cannula coaxial with a stylet;
   a mechanism configured to arm the needle, the mechanism having a platform connected to an arming button with the platform distal of the arming button, the mechanism is configured for sequentially moving the stylet and the cannula from a rest position to a shooting position, with the shooting position characterized by the stylet and the cannula retained in a proximal direction towards a rear end of the body;
   a triggering mechanism configured to release the stylet and subsequently the cannula for displacement from the shooting position to the rest position, with the cannula coupled to a cannula slider having a cannula retaining element configured to maintain the cannula slider in the shooting position, the stylet coupled to a stylet slider having a stylet retaining element configured to maintain the stylet slider in the shooting position, the cannula retaining element separate from the stylet retaining element; and security element located proximal of the arming button, the security element located in the body separate from the stylet slider, the security element including a hook configured to engage with a shoulder of the stylet slider;

wherein a distal portion of the platform is wider than a proximal portion of the platform, with the platform including a curvilinear edge connecting the distal portion of the platform with the proximal portion of the platform;

wherein the curvilinear edge of the platform is configured to interact with a projection formed inside of the body to pivot the platform out of a first position aligned with the cannula side into a second position aligned with the stylet slider.

2. The device according to claim 1, wherein the security element cooperates with the shoulder of the stylet slider to prevent movement of the stylet in the distal direction.

3. The device according to claim 1, wherein the stylet retaining element includes two books arranged symmetrically with a longitudinal axis of the needle.

4. The device according to claim 1, wherein the cannula retaining element includes two hooks arranged symmetrically in relation to a longitudinal axis of the needle.

5. The device according to claim 1, the triggering mechanism includes one trigger provided to unlock the stylet retaining element.

6. The device according to claim 5, wherein the triggering mechanism has two triggers with a first of the two triggers connected to a second of the two triggers by a rod.

7. The device according to claim 1, further comprising a spring placed between the stylet slider and the stylet retaining element.

8. The device according to claim 1, further comprising a spring placed between the cannula slider and the cannula retaining element.

9. The device according to claim 1, wherein the arming button includes a pivot integrated with the arming button, the pivot located between the arming button and the platform.

10. The device according to claim 9, wherein the platform moves about an axis of the pivot.

11. The device according to claim 1, wherein the mechanism configured to arm the needle is configured to prevent simultaneously arming the stylet and the cannula.

* * * * *

UNITED STATES PATENT AND TRADEMARK OFFICE
CERTIFICATE OF CORRECTION

Page 1 of 1

PATENT NO. : 9,113,856 B2
APPLICATION NO. : 13/809908
DATED : August 25, 2015
INVENTOR(S) : David Callede et al.

It is certified that error appears in the above-identified patent and that said Letters Patent is hereby corrected as shown below:

In the Claims:

Claim 1 at Column 9, line 1: "security element" should read "--a-- security element"

Claim 1 at Column 9, line 13: "cannula side" should be changed to "cannula --slide--"

Claim 3 at Column 9, line 19: "two books" should be changed to "two --hooks--"

Claim 5 at Column 10, line 1 should read: "The device according to claim 1, --wherein-- the triggering"

Signed and Sealed this
Nineteenth Day of April, 2016

Michelle K. Lee
*Director of the United States Patent and Trademark Office*